United States Patent [19]

Itoman et al.

[11] Patent Number: 5,697,930
[45] Date of Patent: Dec. 16, 1997

[54] INTRAMEDULLARY NAIL FOR HUMERUS

[75] Inventors: Moritoshi Itoman, Kanagawa-ken; Satoshi Ojima, Tokyo, both of Japan

[73] Assignee: Asahi Kogaku Kogyo Kabushiki Kaisha, Tokyo, Japan

[21] Appl. No.: 593,833

[22] Filed: Jan. 30, 1996

[30] Foreign Application Priority Data

| | | | |
|---|---|---|---|
| Jan. 30, 1995 | [JP] | Japan | 7-12929(P) |
| Oct. 27, 1995 | [JP] | Japan | 7-280163(P) |

[51] Int. Cl.$^6$ ............... A61B 17/72
[52] U.S. Cl. ............... 606/62; 606/64
[58] Field of Search ............... 606/62, 64, 67, 606/72, 95

[56] References Cited

U.S. PATENT DOCUMENTS

| | | |
|---|---|---|
| 2,579,968 | 12/1951 | Rush ............... 606/62 |
| 4,881,535 | 11/1989 | Sohngen. |
| 5,034,013 | 7/1991 | Kyle. |
| 5,041,115 | 8/1991 | Frigg et al. ............... 606/62 |
| 5,472,444 | 12/1995 | Huebner et al. ............... 606/64 |

Primary Examiner—Michael Buiz
Assistant Examiner—David O. Reip
Attorney, Agent, or Firm—Kane,Dalsimer,Sullivan,Kurucz,Levy,Eisele and Richard, LLP

[57] ABSTRACT

An intramedullary nail for a humerus is disclosed which is designed to be inserted in a medullary cavity of a fractured humerus. The nail includes an upper rod portion for location in the upper portion of the humerus and a lower oblique portion for location in the lower portion of the humerus. The upper rod portion is longer than the lower oblique portion, with the lower oblique portion having an oblique axis inclined with respect to the axis of the upper rod portion.

14 Claims, 5 Drawing Sheets

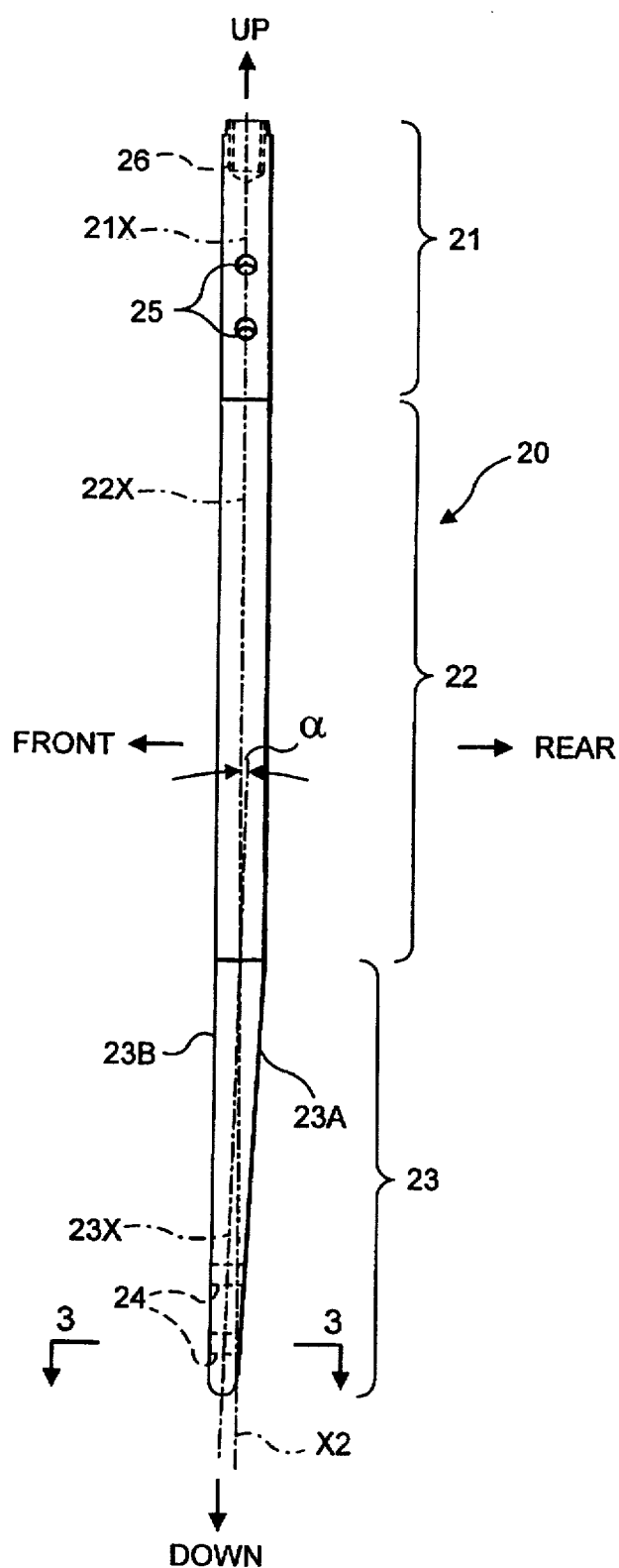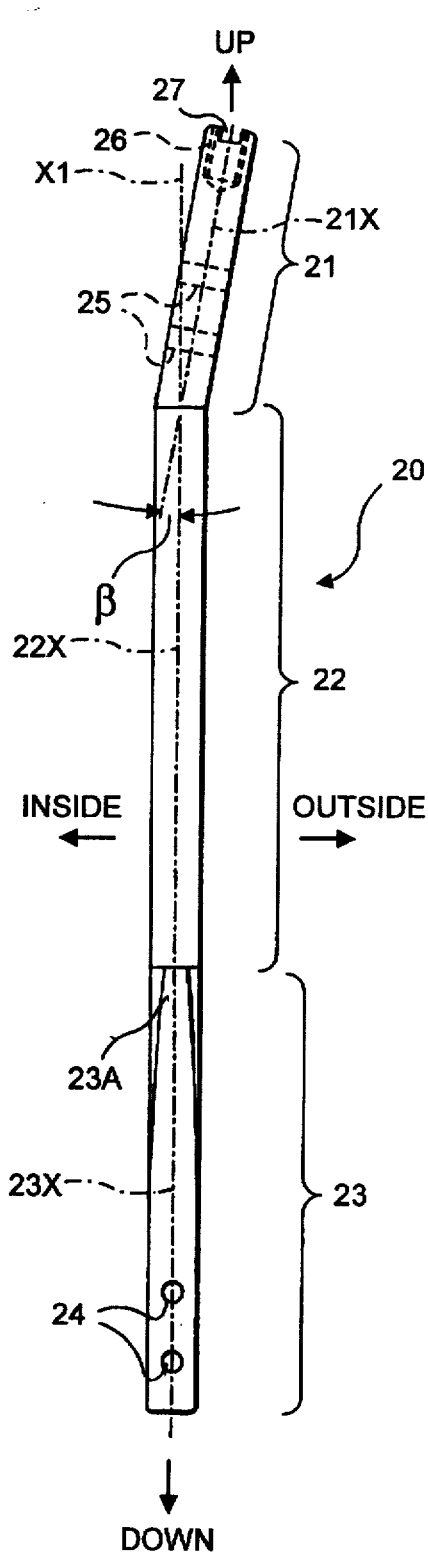
F I G. 1      F I G. 2

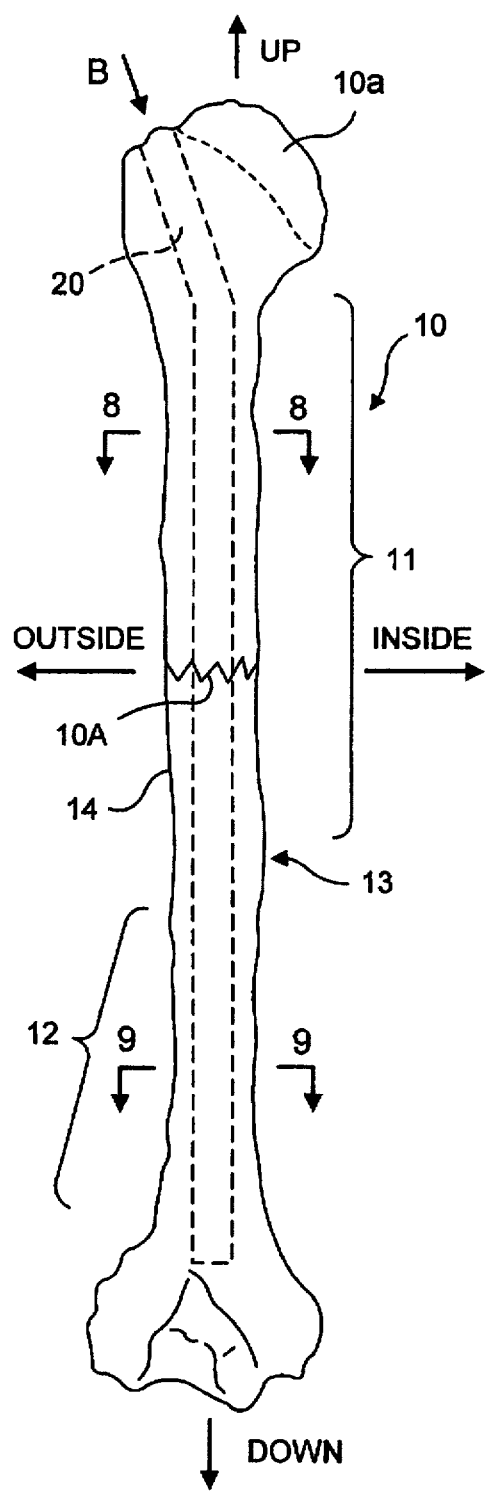
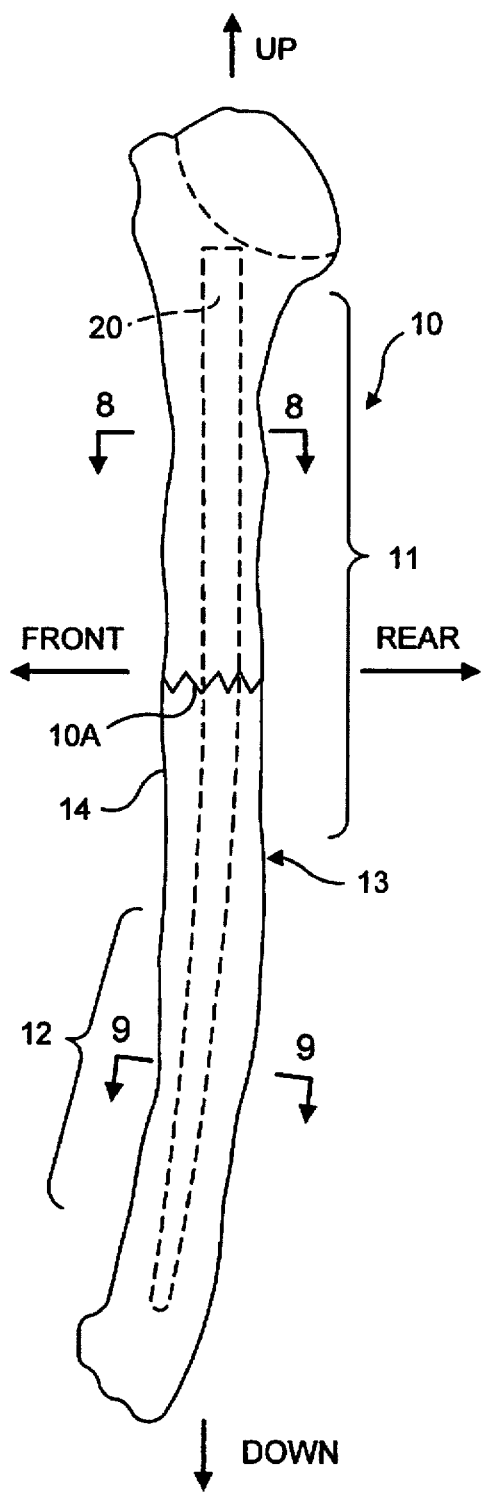
F I G. 6      F I G. 7

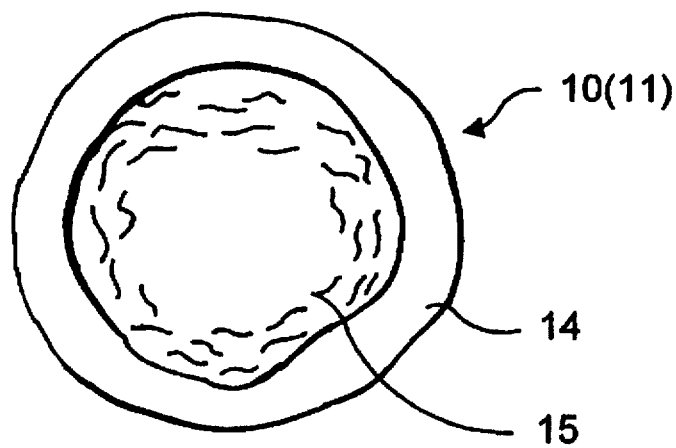
F I G. 8
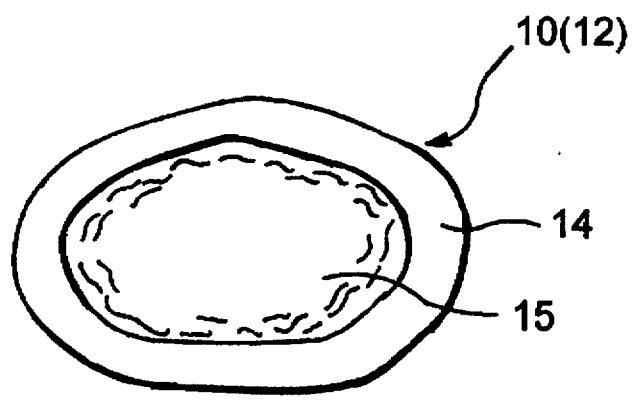
F I G. 9

INTRAMEDULLARY NAIL FOR HUMERUS

BACKGROUND OF THE INVENTION

1. Field of the Invention

The present invention relates to an intramedullary nail for a humerus which can be used to repair a fractured humerus.

2. Description of Related Art

In a known connecting and repairing operation for a fractured bone, an intramedullary nail is inserted in an medullary cavity of the fractured bone from one end thereof while butting the opposed ends of the fractured bone pieces at the fractured section. The intramedullary nail is temporarily secured to the fractured bone to retain the intramedullarynail in the medullary cavity for a predetermined period of time. After the fractured bone pieces are adhered to each other at the butted ends thereof, the intramedullary nail is removed from the medullary cavity. The above-mentioned operation is sometimes applied to the repair of a fractured humerus. In this treatment, intramedullary nails for tibiae have been used as those for the repair of the fractured humerus. However, the intramedullary nail for a tibia is made of a circular rod having a uniform diameter or having a sharp front end. Consequently, it is necessary to enlarge the medullary cavity of the humerus by a reamer in order to insert the intramedullary nail in the medullary cavity. The reaming operation is troublesome and increases the operation time.

SUMMARY OF THE INVENTION

It is an object of the present invention to provide an improved intramedullary nail for a humerus, which needs no or little enlargement operation of the medullar cavity.

According to one aspect of the present invention, there is provided an intramedullary nail for a humerus, which is inserted in a medullary cavity of a fractured humerus while butting the opposed ends of the fractured bones, comprising an upper rod portion which is to be located in an upper portion of the humerus, and a lower oblique portion which is to be located in the lower portion of the humerus and which has an oblique axis inclined with respect to the axis of the upper rod portion, wherein the upper rod portion is longer than the lower oblique portion. Preferably, the inclination angle α of the axis of the upper rod portion with respect to the oblique axis of the lower oblique portion is 0.5° to 5.0°. The humerus is generally inclined at the lower portion thereof forward with respect to the upper portion of the humerus, in the front elevation. To comply with such a shape of the humerus, according to the aspect of the present invention, the intramedullary nail can more suitably follow the shape of the humerus due to the lower oblique portion.

According to a further development of the present invention, to facilitate the insertion of the intramedullary nail in the medullary cavity, the upper rod portion is provided with a uniform diameter portion at one end thereof and a tapered portion whose diameter gradually decreases from the uniform diameter portion toward the lower oblique portion.

According to another development of the present invention, there is provided an intramedullary nail for a humerus, which is inserted in a medullary cavity of a fractured humerus while butting the opposed ends of the fractured bones, comprising an inclined upper rod portion, an intermediate rod portion, and a lower oblique portion, wherein the axis of the inclined upper rod portion is inclined with respect to a plane including the axis of the intermediate rod portion and the axis of the lower oblique portion; the axis of the lower oblique portion is inclined with respect to a plane including the axis of the inclined upper rod portion and the axis of the intermediate rod portion; and the total length of the inclined upper rod portion and the intermediate rod portion is larger than the length of the lower oblique portion.

The axis of the inclined upper rod portion extends in a plane whose phase is preferably different by 90° from the phase of a plane in which the axis of the lower oblique portion extends. There is an articular cartilage at the upper end of the humerus. To prevent the articular cartilage from being injured, it is desirable that the intramedullary nail be inserted in the medullary cavity from the outside of the articular cartilage without interfering with the articular cartilage.

Preferably, the inclination angle β of the axis of the upper rod portion with respect to the plane including the axis of the intermediate rod portion and the axis of the lower oblique portion is less than 20°. Also, the inclination angle α of the axis of the lower oblique portion with respect to the plane including the axis of the upper rod portion and the axis of the intermediate rod portion is preferably 0.5° to 5.0°.

To facilitate the insertion of the intramedullary nail, the intermediate rod portion is preferably made of a tapered shaft whose diameter gradually reduces from the upper end thereof adjacent to the upper rod portion to the lower end thereof adjacent to the lower oblique portion.

According to still further development of the present invention, the lower oblique portion has a cross section which gradually changes from a substantially circular shape at the upper end to a collapsed shape (flat plate shape) at the other end; the substantially flat planes defined by the complete collapse lie perpendicularly to the plane including the axis of the intermediate rod portion (upper rod portion) and the oblique axis of the lower oblique portion; the largest length of the lower rod portion at the front end thereof at which the lower rod portion is collapsed into a substantially flat plate is less than the smallest diameter of the intermediate rod portion. Most preferably, the collapsed shape is an elliptical shape. Nevertheless, if the lower oblique portion is completely collapsed at the lower end, i.e., it is in the form of a substantially flat plate, it can be easily produced. If the lower oblique portion has an elliptical cross section, the tangential planes to the ellipse lie perpendicularly to the plane including the axis of the upper rod portion (intermediate rod portion) and the oblique axis of the lower oblique portion.

The present disclosure relates to subject matter contained in Japanese Patent Application Nos. 7-12929 (filed on Jan. 30, 1995) and 7-280163 (filed on Oct. 27, 1995) which are expressly incorporated herein by reference in their entirety.

BRIEF DESCRIPTION OF THE DRAWINGS

The invention will be described below in detail with reference to the accompanying drawings, in which;

FIG. 1 is a front elevational view of a first embodiment of an intramedullary nail for a humerus according to the present invention;

FIG. 2 is a plan view of FIG. 1;

FIG. 6 is a front elevational view of a humerus;

FIG. 7 is a side view of FIG. 6;

FIG. 8 is a schematic sectional view taken along the line VI—VI in FIG. 6; and,

FIG. 9 is a schematic sectional view taken along the line VII—VII in FIG. 6.

DESCRIPTION OF THE PREFERRED EMBODIMENT

Figure 3:
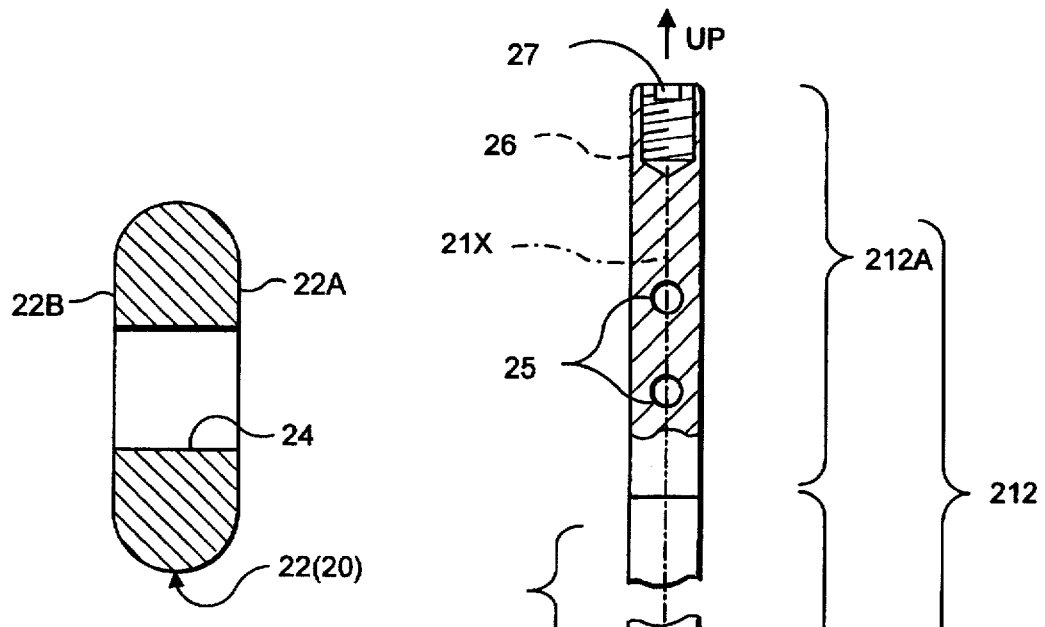
FIG. 3 is a sectional view taken along the line III—III in FIG. 1 or 4.

FIGS. 6 through 9 schematically show a humerus 10. FIGS. 6 and 7 are a front elevational view and a side elevational view of a right humerus, respectively. The humerus 10 extends substantially straight in the front elevational view (FIG. 6) and is provided with a projection of an articular cartilage 10a at the upper end thereof. The humerus 10 is slightly curved in the form of ">" in the side elevational view (FIG. 7). Namely, the humerus 10 is provided with an upper straight portion 11 and a lower oblique portion 12 which is connected to the upper straight portion 11 through an intermediate curved portion 13. In general, the curved portion 13 is located approximately one-third the total length of the humerus 10 from the lower end. The upper straight portion 11 has a generally circular cross section, and the lower oblique portion 12 has a generally elliptical cross section, respectively. The intramedullary nail 20 for a humerus according to the present invention is inserted in the medullary cavity (spongy bone) 15 within the cortex 14 while the ends of the fractured humerus pieces at the fractured section are butted. When the intramedullary nail 20 is inserted, the top end of the lower oblique portion 12 works as a leading portion. Namely, the lower oblique portion 12 is first inserted into the medullary cavity, and then the entire intramedullary nail 20 is gradually inserted.

FIGS. 1 through 3 show a first embodiment of the intramedullary nail 20 according to the present invention. The intramedullary nail 20 is made of metal, such as titanium or stainless steel, etc. The intramedullary nail 20 is provided with an upper rod portion including an inclined upper rod portion 21, and an intermediate rod portion 22, and an inclined lower portion (lower oblique portion) 23. These portions are located in the medullary cavity in this order from the above. The axis 21x of the inclined upper rod portion 21 is inclined by an angle β with respect to a plane including the axis 22x of the intermediate rod portion 22 and the axis 23x of the lower oblique portion 23, i.e., a plane X1 normal to the sheet of FIG. 2. Similarly, the axis 23x of the lower oblique portion 23 is inclined by an angle α with respect to a plane including the axis 21x of the upper rod portion 21 and the axis 22x of the intermediate rod portion 22, i.e., a plane X2 normal to the sheet of FIG. 1. With reference to the intermediate rod portion 22, the axis 21x (direction of the inclination) of the inclined upper rod portion 21 extends in a plane whose phase is different by 90° from the phase of a plane in which the axis 23x (direction of the inclination) of the lower oblique portion 23 extends. The total length of the inclined upper rod portion 21 and the intermediate rod portion 22 is longer than the length of the lower oblique portion 23.

The intramedullary nail 20 according to the first embodiment can be advantageously inserted in the medullary cavity from the outside of the articular cartilage 10a at the upper end of the humerus 10 so as not to interfere with the articular cartilage 10a, as can be seen in FIG. 6. The inclination angle β is preferably less than 20°, and more preferably 5° to 15°. If the angle β is out of the above-mentioned range, it would be in many cases difficult to insert the intramedullary nail in the medullary cavity without interfering with the articular cartilage 10a. The inclination angle α is preferably 0.5° to 5°, and more preferably 1° to 4°. If the angle α is out of the above-mentioned range, the intramedullary nail 20 would not fit the shape of the lower portion of the medullary cavity of the humerus 10.

The inclined upper rod portion 21 is made of a circular rod having a uniform diameter. The intermediate rod portion 22 is made of a tapered rod (shaft) whose diameter gradually decreases from the upper end thereof adjacent to the inclined upper rod portion 21 toward the lower end thereof adjacent to the lower oblique portion 23.

The lower oblique portion 23 is made of a rod whose cross sectional shape is circular at the upper end thereof and is gradually collapsed into a flat plate shape or an elliptical shape. The flat surfaces 23A and 23B of the lower oblique portion 23 are perpendicular to the plane X1 including the axes 22x and 23x of the intermediate rod portion 22 and the lower oblique portion 23. The largest diameter of the lower oblique portion 23 (i.e., the maximum width of the lower or front end of the lower oblique portion 23) is smaller than the smallest diameter of the inclined upper rod portion 21.

The front end of the lower oblique portion 23 and the inclined upper rod portion 21 are provided with two parallel bolt inserting through holes 24 and 25 perpendicular to the axes 23x and 21x of the lower oblique portion 23 and the inclined upper rod portion 21, respectively. The inclined upper rod portion 21 is also provided on the upper end thereof with a threaded hole 26 in which an insertion tool (not shown) can be detachably inserted, and a slot 27.

The intramedullary nail 20 as constructed above is inserted in the medullary cavity 15 of the fractured humerus 10 from the upper end of the cortex 14 of the humerus 10 which has been dissected without interfering with the articular cartilage 10a, while the ends of the fractured humerus pieces are butted at the fractured section 10A (FIGS. 6 and 7). Namely, the intramedullary nail 20 is inserted at the lower oblique portion 23 in the medullary cavity of the humerus 10, with the lower oblique portion 23 being oriented to meet the direction of the inclination of the lower oblique portion 12 of the humerus 10. The intramedullary nail 20 is inserted in the medullary cavity 15 until the lower oblique portion 23 is located within the lower oblique portion 12 of the humerus 10. In this state, the connecting portion (bent portion) between the intermediate rod portion 22 and the lower oblique portion 23 is located in the curved portion 13 of the humerus 10, and the inclined upper rod portion 21 and the intermediate rod portion 22 are located in the upper straight portion 11 of the humerus 10. The insertion can be smoothly carried out due to the lower oblique portion 23 in the form of a collapsed circular rod (substantially flat plate) and the intermediate rod portion in the form of a tapered shaft.

After the close contact of the butted ends at the fractured section 10A is confirmed, bolt inserting through holes corresponding to the bolt inserting through holes 24 and 25 of the lower oblique portion 23 and the upper rod portion 21 are pierced in the humerus 10. Thereafter, bolts are inserted and secured in the bolt inserting through holes of the humerus 10 and the corresponding bolt inserting through holes 24 and 25. Upon insertion of the intramedullary nail 20 in the medullary cavity 15, an inserting tool (not shown) is attached to the threaded hole 26 and the slot 27. The tool is removed after the inserting and securing operation is completed. Upon completion of the connection of the fractured humerus pieces by the intramedullary nail 10, the dissected section is sutured. After a sufficient time to adhere the ends of the fractured humerus pieces at the fractured section 10A, the fractured section is dissected again to remove the bolts inserted in the bolt inserting through holes 24 and 25. Thereafter, the inserting tool is attached to the threaded hole 26 and the slot 27 to withdraw the intramedullary nail 20 from the cortex 14 of the humerus 10, and then the fractured section 10A is sutured again. Thus, the operation is completed.

Note that it is preferable that various intramedullary nails having different lengths of the upper rod portions 21, the intermediate rod portions 22 and the lower oblique portions 23 be prepared and selectively used, depending on the length of the patients' humeri 10.

Figure 4:
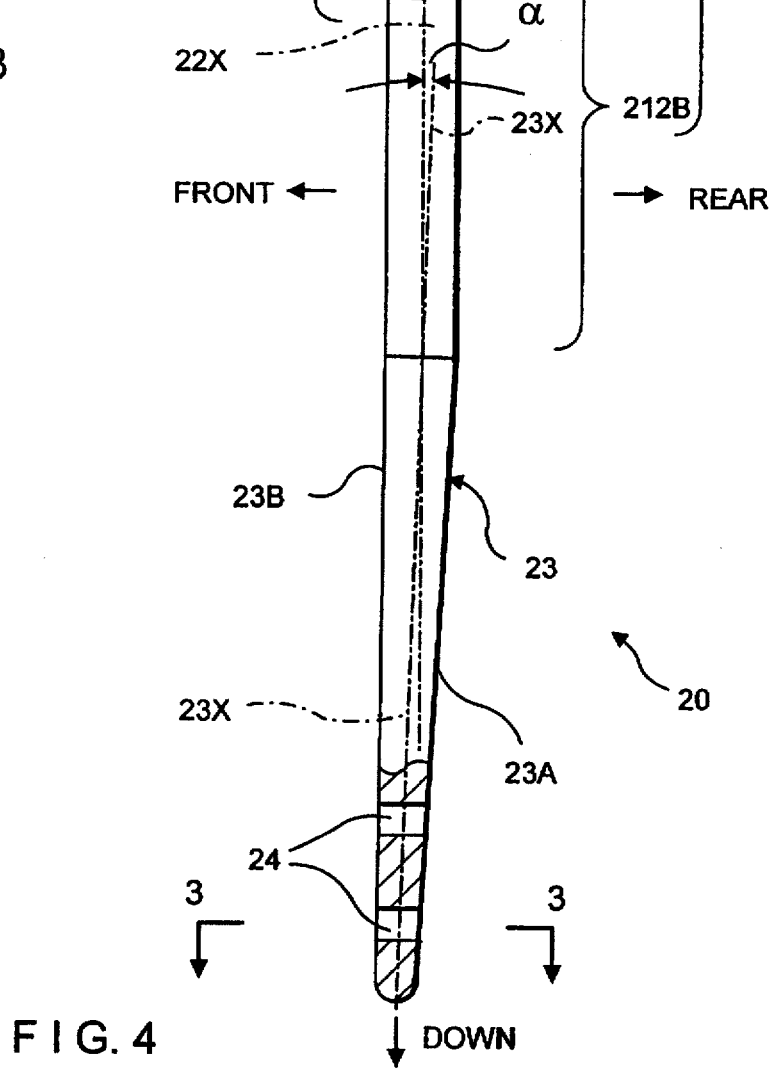
FIG. 4 is a front elevational view of a second embodiment of an intramedullary nail for a humerus according to the present invention.
Figure 5:
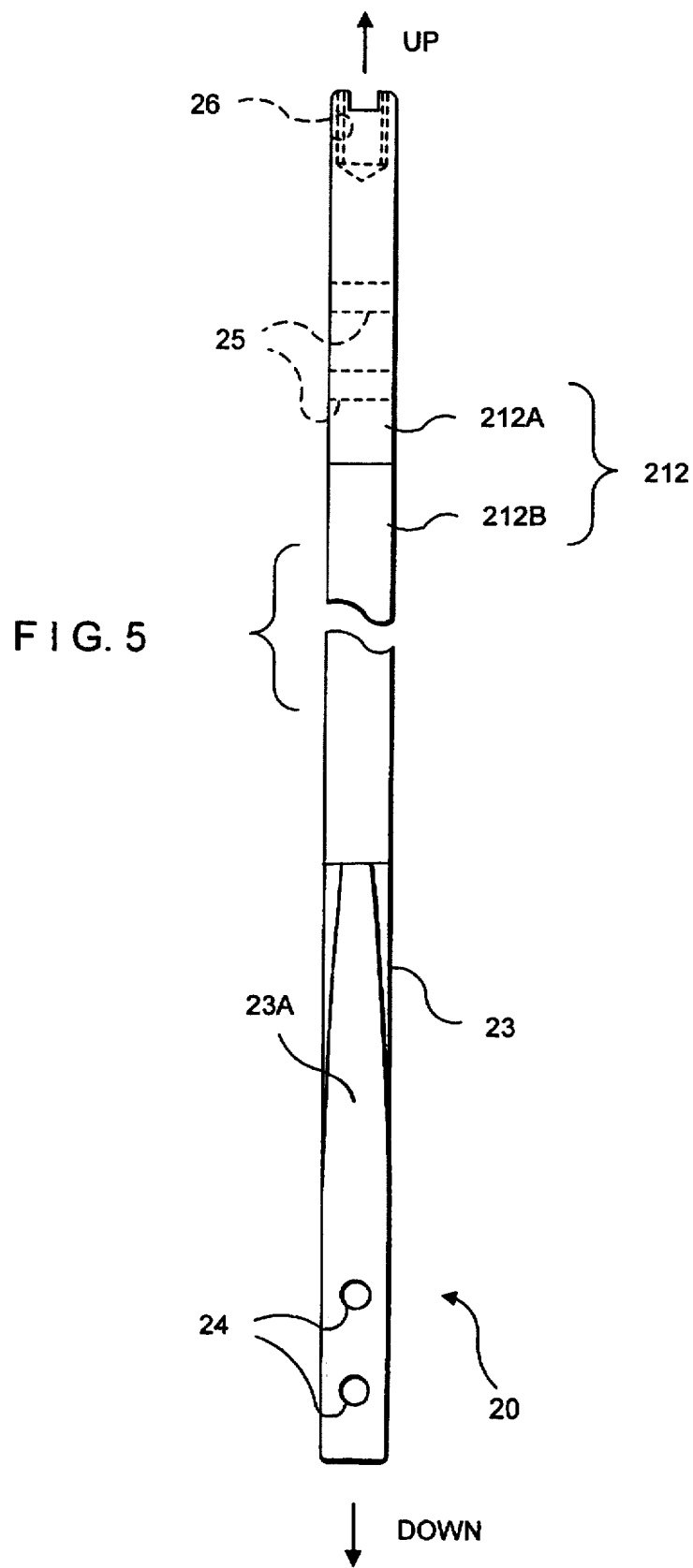
FIG. 5 is a plan view of FIG. 4.

FIGS. 4 and 5 show a second embodiment of an intramedullary nail 20 according to the present invention.

In the second embodiment, the upper rod portion 21 and the intermediate rod portion 22 in the first embodiment illustrated in FIGS. 1 through 3 are replaced with an inclined upper rod portion 212 (upper oblique portion) having a straight axis. Namely, the inclination angle β is zero (β=0). The upper rod portion 212 is comprised of a uniform diameter portion 212A at one end thereof and a tapered shaft portion 212B whose diameter gradually decreases from the uniform diameter portion 212A toward the lower or front end thereof adjacent to the lower oblique portion 23 and which connects the uniform diameter portion 212A and the lower oblique portion 23. Other structure of the second embodiment is the same as that of the first embodiment. In the second embodiment, the elements corresponding to those in the first embodiments are designated with like reference numerals. The intramedullary nail according to the second embodiment can be used particularly for a patient whose articular cartilage 10a would not be injured by the intramedullary nail of which the upper rod portion 21 is not inclined with respect to the intermediate rod portion 22.

Depending on the shape of the humeri, the intramedullary nail having such a straight upper rod portion can be inserted in the medullary cavity without injuring the articular cartilage at the upper end of the associated humerus. The repairing operation of the fractured humerus using the intramedullary nail according to the second embodiment is the same as that in the first embodiment. It is preferable that various intramedullary nails having different lengths of upper rod portions 212 (the uniform diameter portions 212A and the tapered shaft portions 212B) and the lower oblique portions 23 be prepared and selectively used, depending on the length of the humeri 10 of the patients.

Although the lower oblique portion 23 is in the form of a substantially flat plate which is formed by collapsing the circular rod, it is alternatively possible for the lower oblique portion to have an elliptical section which is formed by partly or incompletely collapsing the circular rod. In this alternative, the ratio of the major axis and the minor axis (minor axis/major axis) of the ellipse gradually becomes small from the upper end adjacent to the upper rod portion 21 toward the other end. Or, the lower oblique portion can be made of a tapered rod whose diameter gradually decreases from the upper end thereof toward the lower end or a circular rod having a uniform diameter.

As can be understood from the above discussion, according to the present invention, since the intramedullary nail is shaped to fit the shape of the humerus and particularly the shape of the medullary cavity within the cortex, the intramedullary nail can be easily inserted in the medullary cavity of the humerus, and hence, no or little enlargement operation of the medullary cavity is necessary. This shortens the operation time and eases a burden on a patient.

What is claimed is:

1. An intramedullary nail for a humerus, for insertion in a medullary cavity of a fractured humerus while butting the opposed ends of the fractured bones, comprising, an upper rod portion having an axis which is adapted to be located in an upper portion of the humerus; and, a lower oblique portion which is adapted to be located in a lower portion of the humerus and which has an oblique axis inclined with respect to the axis of the upper rod portion, and said lower oblique portion has a cross section that gradually transforms from a substantially circular shape at the upper end thereof to a substantially elliptical shape at an end opposite to said upper end;

wherein the upper rod portion is longer than the lower oblique portion.

2. An intramedullary nail for a humerus according to claim 1, wherein said upper rod portion is comprised of an inclined upper rod portion and intermediate rod portion; and wherein the axis of said inclined upper rod portion is inclined with respect to a plane including the axis of said intermediate rod portion and the axis of said lower oblique portion.

3. An intramedullary nail for a humerus, according to claim 1, wherein the upper rod portion is provided with a first diameter portion at one end thereof and a tapered portion whose diameter gradually decreases from the first diameter portion to a second diameter portion toward the lower oblique portion.

4. An intramedullary nail for a humerus, according to claim 1, wherein surfaces of the substantially elliptical shape of the opposite end of the lower oblique portion transformation lie perpendicularly to the plane including the axis of the upper rod portion and the axis of the lower oblique portion.

5. An intramedullary nail for a humerus, according to claim 4, wherein a major length of the lower oblique portion at a front end thereof at which the lower rod portion is transformed into an elliptical sectional shape is less than the second diameter of the upper rod portion.

6. An intramedullary nail for a humerus, according to claim 1, wherein the inclination angle of the axis of the upper rod portion with respect to the oblique axis of the lower oblique portion is 0.5° to 5.0°.

7. An intramedullary nail for a humerus, which is adapted to be inserted in a medullary cavity of a fractured humerus while butting the opposed ends of the fractured bones, comprising, an inclined upper rod portion having an axis;

an intermediate rod portion having an axis; and, a lower oblique portion having an axis;

wherein the axis of the upper rod portion is inclined with respect to a plane including the axis of the intermediate rod portion and the axis of the lower oblique portion;

the axis of the lower oblique portion is inclined with respect to a plane including the axis of the upper rod portion and the axis of the intermediate rod portion; and the total length of the upper rod portion and the intermediate rod portion is larger than the length of the lower oblique portion.

8. An intramedullary nail for a humerus, according to claim 7, wherein the inclination angle β of the axis of the upper rod portion with respect to the plane including the axis of the intermediate rod portion and the axis of the lower oblique portion is less than 20°, and the inclination angle α of the axis of the lower oblique portion with respect to the plane including the axis of the upper rod portion and the axis of the intermediate rod portion is 0.5° to 5.0°.

9. An intramedullary nail for a humerus, according to claim 7, wherein the axis of the upper rod portion extends in a plane whose phase is different by 90° from the phase of a plane in which the axis of the lower oblique portion extends.

10. An intramedullary nail for a humerus, according to claim 7, wherein the intermediate rod portion is made of a tapered shaft whose diameter gradually reduces from an upper end thereof adjacent to the upper rod portion to a lower end thereof adjacent to the lower oblique portion.

11. An intramedullary nail for a humerus, according to claim 7, wherein the lower oblique portion has a cross section which gradually changes from a substantially circular shape at an upper end to a non-circular shape at a lower end.

12. An intramedullary nail for a humerus, which is adapted to be inserted in a medullary cavity of a fractured humerus while butting the opposed ends of the fractured bones, comprising, an upper rod portion having a first circular cross section which is adapted to be located in an upper portion of the humerus; and, a lower rod portion which is adapted to be located in the lower portion of the humerus, said lower portion having a cross section that gradually transforms from a circular cross-section at the upper end thereof to a substantially elliptical cross section at the end opposite to said upper end.

13. An intramedullary nail for a humerus, according to claim 12 further comprising an intermediate tapered rod portion extending between said upper rod portion and said lower rod portion, said intermediate rod portion having said first circular cross section at an upper end thereof and a second circular cross-section at a lower end thereof.

14. An intramedullary nail for a humerus, according to claim 13 wherein said first circular cross section is greater in diameter than said second circular cross section.

* * * * *